United States Patent [19]

Hansen et al.

[11] Patent Number: 5,017,571
[45] Date of Patent: May 21, 1991

[54] CARBAMIC ACID ESTER OF SUBSTITUTED 7-HYDROXY-2,3,4,5-TETRAHYDRO-1H-3-BENZAZEPINES

[75] Inventors: Kristian T. Hansen, Soborg; Hans Bundgaard, Horsholm; Peter Faarup, Vaerlose, all of Denmark

[73] Assignee: Novo Nordisk A/S, Bagsvaerd, Denmark

[21] Appl. No.: 317,016

[22] Filed: Feb. 28, 1989

[30] Foreign Application Priority Data

Mar. 1, 1988 [DK] Denmark .......................... 1076/88

[51] Int. Cl.$^5$ .................... C07D 223/16; A61K 31/55
[52] U.S. Cl. .................................. 514/213; 540/594; 540/595
[58] Field of Search ................ 540/594, 595; 514/213

[56] References Cited

U.S. PATENT DOCUMENTS

| | | | |
|---|---|---|---|
| 3,393,192 | 7/1968 | Walter et al. | 540/595 |
| 3,609,138 | 9/1971 | Mull et al. | 540/595 |
| 4,011,319 | 3/1977 | Kaiser et al. | 514/213 |
| 4,284,555 | 8/1981 | Gold et al. | 540/595 |
| 4,751,222 | 6/1988 | Braestrup et al. | 514/213 |

FOREIGN PATENT DOCUMENTS

| | | |
|---|---|---|
| 5300 | of 1979 | European Pat. Off. . |
| 0170090 | 2/1986 | European Pat. Off. . |
| 0200455 | 11/1986 | European Pat. Off. . |

OTHER PUBLICATIONS

Charton, M., "Prodrug Liability Prediction through the use of Substituent Effects", *Methods in Enzymology*, vol. 112 (1985), pp. 323-340.

*Primary Examiner*—Mukund J. Shah
*Assistant Examiner*—Philip Datlow
*Attorney, Agent, or Firm*—Gordon W. Hueschen

[57] ABSTRACT

Compounds having the formula

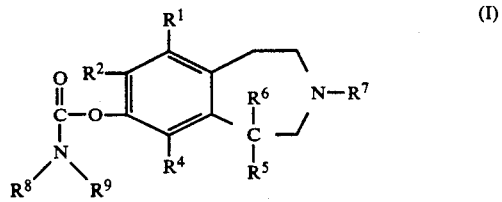

(I)

wherein $R^1$, $R^4$, $R^6$, $R^7$, and $R^8$ are hydrogen or a substituent, $R^2$ is a substituent, $R^5$ is an optionally-substituted bicyclic ring system, especially a 7-benzofuranyl or 2,3-dihydrobenzofuran-7-yl substituent, $R^9$ is hydrogen, alkyl, alkoxycarbonyl or, together with $R^8$, forms the remainder of a heterocyclic ring, their pharmaceutically-accceptable salts, as well as their pharmaceutical compositions and use as prodrugs for compounds active for the treatment of mental disorders, are disclosed.

10 Claims, No Drawings

CARBAMIC ACID ESTER OF SUBSTITUTED 7-HYDROXY-2,3,4,5-TETRAHYDRO-1H-3-BENZAZEPINES

This invention relates to novel carbamic acid esters of substituted 7-hydroxy-2,3,4,5-tetrahydro-1H-3- benzazepines which are useful prodrugs for treatment of mental disorders. As used in this specification the term "prodrug" is defined as a derivative of a biologically active compound, which derivative, when absorbed into the blood stream of animals and humans, decomposes in such manner as to release the active substance and permits the latter to attain a higher bioavailability than that which would be obtained if the active substance, per se. was administered perorally. Thus, the active substance can be administered without problems intravenously; however, peroral administration is usually preferred for obvious reasons. Peroral administration of the active substance is often unsatisfactory, as it is decomposed in the gastrointestinal tract and during the first pass through the liver; but peroral administration of the prodrug has both the advantage of an easy administration and a high bioavailability.

Applicant's European patent application No. 86303001 describes 2,3,4,5-tetrahydro-1H-3-benzazepines useful in the treatment of mental disorders. If administered intravenously, these benzazepines are very useful in the treatment of mental disorders, as described in the European patent application; however, if administered orally they suffer from the disadvantage that very large doses have to be given in order to obtain the wanted effect.

Thus, a need exists for a measure, by means of which the benzazepines described in European patent application No. 86303001 can be administered orally in much smaller doses and yet generate the wanted effect.

Now, according to the invention it has been found that a selected category of the benzazepines described in European patent application No. 86303001, i.e. the category carrying a (phenolic) hydroxy group at the position No. 7 in the benzazepine nucleus (corresponding to the case of $R^3$ being hydroxy in the terminology of the European patent application) can be converted to useful prodrugs, if certain selected carbamic acid esters are formed of the members belonging to this selected category of benzazepines.

Thus, the carbamic acid esters of substituted 7-hydroxy-2,3,4,5-tetrahydro-1H-3-benzazepines according to the invention have the general formula I

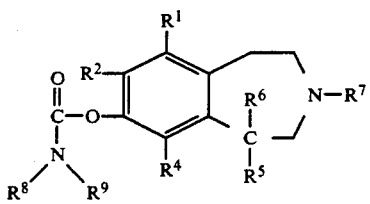

(I)

wherein
$R^1$ is H, halogen, or $C_{1-4}$ alkyl
$R^2$ is halogen, $CF_3$, CN
$R^4$ is H, or halogen
$R^5$ is furyl, thienyl, pyridyl, or ring systems consisting of phenyl ortho condensed with a benzen, cyclohexan, cyclohexen, cyclopentan or cyclopenten ring in which rings one of the carbon atoms may be exchanged with oxygen, sulphur or nitrogen, and each of these ring systems optionally are substituted with halogen, hydroxy or alkoxy with or not more than 4 carbon atoms,
$R^6$ is H or $CH_3$
$R^7$ is H or $C_{1-4}$ alkyl
$R^8$ is H, alkyl, alkenyl, aralkyl, cycloalkyl, or aryl
$R^9$ is H, or $R^9$ together with form a
piperidino, pyrrolidinyl, morpholino, or piperazinyl ring or a ring with the formula

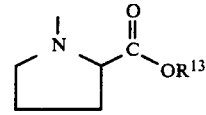

or $R^9$ can be alkyl or alkoxycarbonyl with the formula

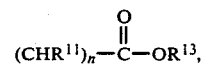

wherein n is 0 is 1, where $R^{11}$ is H, $C_3$, $(CH_3)_2CH$, $CH_2CH(CH_3)_2$,

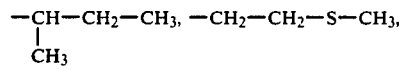

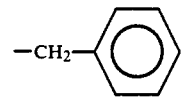

and $R^{13}$ is H, alkyl, cycloalkyl, aralkyl, or a 2-acetamide group with the formula

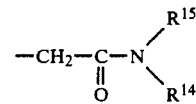

where
$R^{15}$ is H, $C_3$, $C_2H_5$, $C_3H_8$, or $CH(CH_3)_2$, and
$R^{14}$ is H, $CH_3$, $C_2H_5$, $C_3H_8$ or $CH(CH_3)_2$,
and pharmaceutical-acceptable salts thereof.

In a preferred embodiement of the esters according to the invention $R^1$ represents hydrogen. Such esters are easily synthesized.

In a preferred embodiment of the esters according to the invention $R^2$ is halogen, preferably chloro or fluoro. The corresponding parent substance exhibits a very high affinity to the receptor.

In a preferred embodiment of the esters according to the invention $R^4$ is hydrogen. Such esters are easily synthesized.

In a preferred embodiment of the esters according to the invention $R^5$ is phenyl ortho condensed with a benzen, cyclohexan, cyclohexen, cyclopentan or cyclopenten ring which may be substituted with halogen, hydroxy or methoxy. Due to the big and lipophile $R^5$ moieties the pharmacological effect is very potent.

In a preferred embodiment of the esters according to the invention $R^5$ is benzofuranyl or 2,3-dihydrobenzofuranyl. Due to the big and lipophile $R^5$ moieties the pharmacological effect is very potent.

In a preferred embodiment of the esters according to the invention $R^5$ is benzothienyl or 2,3-dihydrobenzothienyl. Due to the big and lipophile $R^5$ moieties the pharmacological effect is very potent.

In a preferred embodiment of the esters according to the invention $R^5$ is furyl, thienyl or pyridyl. Due to the big and lipophile $R^5$ moieties the pharmacological effect is very potent.

In a preferred embodiment of the esters according to the invention $R^5$ is chromanyl or chromenyl. Due to the big and lipophile $R^5$ moieties the pharmacological effect is very potent.

In a preferred embodiment of the esters according to the invention $R^5$ is indolyl or indolinyl. Due to the big and lipophile $R^5$ moieties the pharmacological effect is very potent.

In a preferred embodiment of the esters according to the invention $R^5$ is quinolinyl. Due to the big and lipophile $R^5$ moieties the pharmacological effect is very potent.

In a preferred embodiment of the esters according to the invention $R^6$ represents hydrogen. Such esters are easily synthesized.

In a preferred embodiment of the esters according to the invention $R^7$ is hydrogen, methyl, or cyclopropyl. Such esters exhibit a potent pharmacological effect.

In a preferred embodiment of the esters according to the invention $R^8$ is alkyl and $R^9$ is H, alkyl, or alkoxy carbonyl.

In a preferred embodiment of the esters according to the invention and $R^9$ together form a ring with the formula

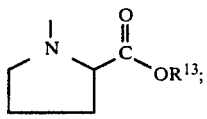

where $R^{13}$ is alkyl, preferably $C_1$-$C_5$-alkyl, or an N,N-di ($C_{1-5}$-alkyl)2-acetamide group

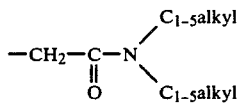

Also, the invention comprises a pharmaceutical composition containing an ester of formula I according to the invention or a salt thereof, in solid form for oral administration The pharmaceutical composition is usually prepared as a tablet or a capsule, preferably as an enteric coated tablet.

Also, the invention comprises a use of a composition according to the invention as a neurolepticum.

In a preferred embodiment of the use of a composition according to the invention the use is for, the treatment of schizophrenia, other psychoses, and manic depressive disorders.

Also, the invention comprises a process for preparing esters of formula I or salts thereof, characterized by reacting a benzazepine compound of the general formula II

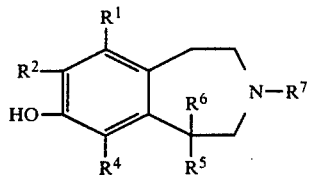

with an activated carbamic acid (III) of the formula

preferably the acid halide

where X is a halogen, preferably chloride, or with one or two isocyanates V

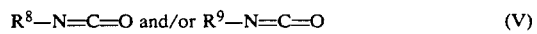

whereafter (I) is isolated and if wanted converted to a salt.

As appears from the above, several active centers can be present in the carbamic acid esters according to the invention. It is to be understood that the invention comprises both racemates and all optical isomers.

The new compounds may be synthesized by esterification of the 7-hydroxy-benzazepine with an active carbamic acid derivative. In order to synthesize the new compounds also various new intermediates have been synthesized according to methods published in the literature. Thus, carbamoyl chlorides of N-substituted amino pro-moieties are prepared by reacting the actual N-substituted amino compound in its base form with phosgene in a suitable organic solvent (vide e.g. J.Org.Chem., 51, 1986, 3494–3498), and isocyanates of unsubstituted amino pro-moieties are generally prepared by reacting the amino compound in its base form with the diphosgene reagent trichloromethyl chloroformate (TCF, e.g. J.Org.Chem. 41, 1976, 2070–71; Org.Synth., 59, 1979, 195–201). The identity of these pro-moiety intermediates are confirmed by microanalysis, IR, and $^1$H NMR spectroscopy.

In European patent application No. 170 090 it is stated in the paragraph bridging pages 4 and 5 that there is no way to accurately predict which prodrug structure will be suitable for a particular drug, and that a derivative which will work well for one drug may not do so for another, as differences in absorption, metabolism, distribution, and excretion among drugs do not permit generalizations to be made about prodrug design. Also, from page 34 in this European patent application No. 170 090 it appears that different (but related) parent substances with the same prodrug moiety exhibit widely varying relative bioavailabilities, which confirms the above finding that there is no way to accurately predict which prodrug structure will be suitable for a particular drug, even if a similar drug is known to exhibit a satisfactory relative bioavailability with a specific prodrug structure.

Thus, even if it appears from U.S. Pat. No. 4,284,555 that a certain class of benzazepines can be esterified with carbamic acid esters to form prodrugs with improved relative bioavailability, the parent substances in this invention (the previously described subgroup of the benzazepines described in European patent application No. 86303001) differ significantly from the benzazepines described in U.S. Pat. No. 4,284,555, and thus there would be no accurate way to predict which kind of prodrug structure would be suitable for the parent substances in the invention.

The prodrug effect is measured as the ratio between the area under the curve representing the concentration of the parent substance in the blood stream versus time in case of oral administration of the prodrug and the corresponding area in case of intravenous administration of an equimolar amount of the corresponding parent compound. In the sense of this invention the parent compound corresponding to a certain prodrug is a compound related to the prodrug, the only difference being that the position No. 7 in the parent compound carries the unesterified phenolic hydroxy group only. It has been found that mainly the parent compound is found in the blood stream if the prodrug is administered orally.

For more detailed information in regard to prodrug definition reference can be made to A. A. Sinkula and S. H. Yalkowsky; J.Pharm.Sci., 64, 1975, 183–210, H. Bundgaard (ed.) (1985), Design of Prodrugs, Elsevier, Amsterdam, E. B. Roche (ed.) 1977, Design of Biopharmaceutical Properties through Prodrugs and Analogs, American Pharmaceutical Association, Washington D.C.

More precisely, the prodrug effect of the bioavailability is measured in the following manner.

The prodrug is administered perorally to a test animal and in a total dose designated "$dose_{p.o.}$". The concentration of the parent substance in the blood in mg of parent substance/ml of plasma is measured at regular time intervals after administration, and a curve representing this concentration versus time, e.g. in hours, is drawn up. The area under the curve ($AUC_{p.o.}$) in (mg/ml) x minutes is calculated.

Similarly the parent substance is administered intravenously in a total dosis designated "$dose_{i.v.}$". A similar curve is drawn up, and the area below this curve is similarly "$AUC_{i.v.}$".

Now, the bioavailability F is calculated according to the formula $$F = \frac{AUC_{p.o.}/dose_{p.o.}}{AUC_{i.v.}/dose_{i.v.}} \cdot 100\%$$

More specifically, in relation to this invention the bioavailability of the prodrugs is measured in dogs.

In a cross-over study parent substance and corresponding prodrug are administered with an interval of one week, the parent substance as an intravenous bolus and the corresponding prodrug as an oral solution respectively.

By means of solid phase extraction of the plasma samples and HPLC the plasma concentration of both parent substance and prodrug is estimated up to 24 hours after administration. After the examples illustrating the synthesis of the prodrugs findings in regard to the bioavailability of some of the exemplified prodrugs and some prodrugs chemically related thereto will be presented.

The invention will be further illustrated by the following examples.

EXAMPLE 1

(+)-8-chloro-7-[(N N-dimethylamino)carbonyloxy]-5-(7-benzofuranyl)-2,3,4,5-tetrahydro-1H-3-methyl-3-benzazepine, HCl.

1.0 g (3.04 mmol) of the parent substance ((+)-8-chloro7-hydroxy-5-(7-benzofuranyl)-2,3,4,5-tetrahydro-1H-3-methyl3-benzazepine) was dissolved in 20 ml of dry pyridine. To this solution was added in a single operation 0.56 ml (6.08 mmol) of N,N-dimethyl carbamoyl chloride. The thus obtained mixture was placed on an oil bath and refluxed for 24 hours. Pyridine was evaporated in vacuo together with excess of reagent. The residual material was dissolved in 30.0 ml of dry ether and precipitated with a 1.0 N HCl solution in ether. The white precipitate was washed with 2×10 ml of dry ether. Drying in the presence of $P_2O_5$ was performed for 24 hours at 0.2 mm Hg.

The purity of the product in this example and in Examples 2–6 was determined by means of a HPLC method see below.

The synthesized compound was chromatographed on a Nucleosil RP C-18 silica support (mean particle size 5 μm) column by means of a step gradient procedure. The eluent program was initiated with a mixture of 25% of acetonitrile and 75% of a 0.1M ammonium sulphate buffer of pH 3.0. By means of two steps the acetonitrile volume fraction of the eluent was raised to 55%. Detection of the column outflow was performed by means of UV absorbance.

Purity according to HPLC >98%. The product peak corresponds to a retention time of 16.0 minutes.

$^1$H-NMR,δppm. (CDCl$_3$, TMS): 2.36 3H(s); 3.00 6H(s); 2.70–3.30 6H(m); 4.60 1H(t); 6.10 1H(s); 6.70–7.55 6H(m);

EXAMPLE 2

(+)-8-chloro-7-[(N,N-diethylamino)carbonyloxy]-5-(7-benzofuranyl)-2,3,4,5-tetrahydro-1H-3-methyl-3-benzazepine, HCl.

0.5 g (1.52 mmol) of ((+)-8-chloro-7-hydroxy-5-(7-benzofuranyl)-2,3,4,5-tetrahydro-1H-3-methyl-3-benzazepine) was dissolved in 20 ml dry pyridine. To this solution was added in one operation 0.39 ml (3.04 mmol) N,N-diethyl carbamoyl chloride. The thus obtained mixture was placed on an oil bath and refluxed for 24 hours. Pyridine was evaporated in vacuo together with excess of reagent. The residual material was dissolved in 20 ml of dry ether and precipitated with a 10% excess of 1N HCl solution in ether. The white precipitate was washed with 2×10 ml of dry ether. Drying with $P_2O_5$ was performed for 24 hours at 0.2 mm Hg.

Purity according to HPLC >98%. The product peak corresponds to a retention time of 24.0 minutes.

$^1$H-NMR,δppm. (CDCl$_3$, TMS): 1.15 6H(m); 2.84 3H(s): 2.9–4.2 6H(m); 3.30 4H(m); 5.48 1H(s); 6.30 1H(s); 6.84–7.70 6H(m); 2.9–4.2 6H(m).

EXAMPLE 3

(+)-8-chloro-7-[(N-methyl-N-ethoxycarbonyl)amino carbonyloxy]-5-(7-benzofuranyl)-2 3 4 5-tetrahydro-1H-3-methyl-3-benzazepine, HCl.

0.98 g (3.0 mmol) of (+)-8-chloro-7-5-(7-benzofuranyl)- 2,3,4,5-tetrahydro-1H-3-methyl-3-benzazepine was dissolved in 10 ml dry pyridine. This solution was added dropwise and at room temperature to a solution of 1.5 g (9 mmol) of N- methyl-N-chloroformyl ethyl carbamate in 5 ml of dry pyridine. The thus obtained mixture was placed on an oil bath and refluxed for 16 hours. Pyridine was evaporated in vacuo together with excess of reagent. The residual material was dissolved in 20 ml of dry ether and precipitated with 10% excess of IN HCl dissolved in ether. The white precipitate was washed twice with 10 ml of dry ether.

Purity according to HPLC >98%. The product peak corresponds to a retention time of 15.8 minutes.

$^1$H-NMR,δppm. (CDCl$_3$, TMS): 1.30 3H(t); 2.96 3H(s); 3.28 3H(s); 4.25 2H(q); 2.9–4.2 6H(m); 5.50 1H(s); 6.30 1H(s); 6.85–7.70 6H(m).

EXAMPLE 4

(+)-8-chloro-7-[(R,S)-N-(1-methoxycarbonyl-1-ethyl-)amino carbonyloxy]-5-(7-benzofuranyl)-2,3,4,5-tetrahydro-1H-3-methyl-3-benzazepine.

0.40 g (3.05 mmol) of N-carbonyl D,L alanine methyl ester is dissolved in 5 ml acetonitrile. This solution was added dropwise to a refluxing solution of 0.50 g (1.52 mmol) of (+)-8-chloro-7-hydroxy-5-(7-benzofuranyl)-2,3,4,5-tetrahydro-1H-3-methyl-3-benzazepine in 20 ml of acetonitrile, and reflux is continued for further 8 hours. Acetonitrile and excess of reagent was evaporated in vacuo, leaving a yellow oil, which was easily purified by flash chromatography on a silica column and evaporated in vacuo to a white crystalline compound.

Purity according to HPLC >98%. The product peak corresponds to a retention time of 14.3 minutes.

$^1$H-NMR,δppm. (CD$_3$-SO-CD$_3$, TMS): 1.25 3H(8d); 2.28 3H(s); 2.80–4.20 8H(m); 3.56 3H(s); 4.80 1H(d); 6.30 1H(s); 7.0–8.0 6H(m).

EXAMPLE 5

(+)-8-chloro-7-[(S)(2-methoxycarbonyl)-1-pyrrolidinyl-carbonyloxy]-5-(7-benzofuranyl)-2,3,4,5-tetrahydro-1H-3-methyl-3-benzazepine.

A solution of 0.58 g (3.05 mmol) of N-chlorocarbonyl L-proline methyl ester in 10 ml of dry pyridine was dropwise added to 0.5 g (1.52 mmol) of (+)-8-chloro-7-hydroxy-5-(7-benzofuranyl)-2,3,4,5-tetrahydro-1H-3-methyl-3-benzazepine in 10 ml of dry pyridine. When the addition was complete, the mixture was placed on an oil bath for 16 hours with reflux. Pyridine and excess of reagent was evaporated in vacuo, and the residual material was taken into 50 ml of ether, and washed with 5% NaHCO$_3$, saturated NaCl and H$_2$O. The ether phase was dried over MgSO$_4$ and evaporated to an oil. The residual oil was purified on a silica column by means of flash chromatography, and after vacuum evaporation of the eluent a white crystalline compound was obtained.

Purity according to HPLC >98%. The product peak corresponds to a retention time of 18.5 minutes.

$^1$H-NMR, ppm. (CDCl$_3$, TMS): 1.50–4.50 19H(m,complex); 4.80 H(d); 6.40 1H(d); 6.80–7.70 6H(m).

EXAMPLE 6

(+)-8-chloro-7-(isopropylamino carbonyloxy)-5-(7-benzofuranyl)-2,3,4,5-tetrahydro-1H-3-methyl-3-benzazepine To a refluxing mixture of 0.5 g(1.52 mmol) of (+)-8-chloro-7-hydroxy-5-(7-benzofuranyl)-2,3,4,5-tetrahydro-1H-3-methyl-3-benzazepin in 20 ml acetonitrile was dropwise added 0.30 ml (3.04 mmol) isopropyl isocyanate. The mixture was refluxed for additional 6 hours, and then the acetonitrile was removed by evaporation in vacuo. The residual material was obtained as analytically pure crystals from hot isopropanol.

Purity according to HPLC >98%. The product peak corresponds to a retention time of 17.5 minutes.

$^1$H-NMR,δppm. (CD$_3$SOCD$_3$, TMS): 1.00 6H(d); 2.20 3H(s); 2.10–3.50 8H(m); 4.80 1H(s); 6.25 1H(s); 6.8–7.9 6H(m).

In analogy with the preparation described in example 6 the following compounds were synthesized:

EXAMPLE 7

(+)-8-chloro-7-(allylamino carbonyloxy)-5-(7-benzofuranyl)2,3,4,5-tetrahydro-1H-3-methyl-3-benzazepine $^1$H-NMR,δppm. (CDCl$_3$, TMS): 2.35, 3H(s); 2.4–3.3 6H(m); 3.8 2H(t); 4.8 1H(t); 5.0–5.2 3H(m); 5.8 1H(m); 6.4 1H(s); 6.78 1H(s); 7.05 1H(d); 7.25 2H(m); 7.55 2H(m).

EXAMPLE 8

(+)-8-chloro-7-(benzylamino carbonyloxy)-5-(7-benzofuranyl)-2,3,4,5-tetrahydro-1H-3-methyl-3-benzazepine by heating to 70° C. in toluene with 0.5 equiv. of N-methylpiperidine as catalyst.

$^1$H-NMR,δppm. (CDCl$_3$, TMS): 2.3 3H(s); 2.4–3.4 6H(m); 4.85 1H(d); 5.1–5.3 3H(m); 6.5 1H(s); 6.8 1H(s); 7.0–7.6 10H(m).

EXAMPLE 9

(+)-8-chloro-7-(n-butylamino carbonyloxy)-5-(7-benzofuranyl)-2,3,4,5-tetrahydro-1H-3-methyl-3-benzazepine by heating to 70° C. in toluene with 0.2 equiv. of N-methylpiperidine as catalyst.

$^1$H-NMR,δppm. (CDCl$_3$, TMS): 1.2 7H(m); 2.3 3H(s); 2.4–3.3 6H(m); 4.7 1H(d); 5.0–5.2 3H(m); 6.4 1H(s); 6.8 1H(d); 7.05 1H(d); 7.25 2H(m); 7.6 2H(m).

EXAMPLE 10

(+)-8-chloro-7-(cyclohexylamino carbonyloxy)-5-(7-benzofuranyl)-2,3,4,5-tetrahydro-1H-3-methyl-3-benzazepine by refluxing 24 h in methylenechloride with 1 equiv. of triethylamine as catalyst.

$^1$H-NMR,δppm. (CD$_3$SOCD$_3$, TMS): 1.0–1.8 10H(m); 2.15 1H(m); 2.25 3H(s); 2.6–3.2 5H(m); 3.7 1H(m); 4.6 1H(d); 6.2 1H(s); 6.8 2H(m); 7.15 2H(m); 7.6 2H(m).

In analogy with the preparation described in example 4 the following compounds were synthesized:

EXAMPLE 11

(+)-8-chloro-7-[(S)-N-(1-methoxycarbonyl-phenethyl-)amino carbonyloxy]-5-(7-benzofuranyl)-2,3,4,5-tetrahydro-1H-3-methyl-3-benzazepine $^1$H-NMR,δppm. (CDCl$_3$, TMS): 2.25 3H(s); 2.4–3.2 6H(m); 3.8–4.1 4H(s,m); 4.55 1H(d); 5.1 2H(m); 6.3 1H(s); 6.75 2H(m); 7.15 2H(m); 7.55 2H(m).

EXAMPLE 12

(+)-8-chloro-7-[(S)-N-(1-methoxycarbonyl-2-methyl-butyl)amino carbonyloxy]-5-(7-benzofuranyl)-2,3,4,5-tetrahydro-1H-3-methyl-3-benzazepine $^1$H-NMR,δppm. (CDCl$_3$, TMS): 1.2–1.5 9H(m); 2.3 3H(s); 2.4–3.2 6H(m); 3.8–4.3 4H(s,m); 4.55 1H(d); 5.2 2H(m); 6.3 1H(s); 6.7 2H(m); 7.3 2H(m); 7.6 2H(m).

EXAMPLE 13

(+)-8-chloro-7-[(R,S)-N-(1-methoxycarbonyl-3-methyl-butyl)amino carbonyloxy]-5-(7-benzofuranyl)-2,3,4,5-tetrahydro-1H-3-methyl-3-benzazepine $^1$H-NMR,δppm. (CDCl3, TMS): 1.2–1.5 9H(m); 2.3 3H(s); 2.4–3.2 6H(m); 3.8–4.3 4H(s,m); 4.6 1H(d); 5.3 2H(m); 6.5 1H(s); 6.7 2H(m); 7.3 2H(m); 7.7 2H(m).

In analogy with the preparation described in example 2 the following compounds were synthesized:

EXAMPLE 14

(+)-8-chloro-7-[(N,N-dimethylamino)carbonyloxy]-5-(2,3-dihydrobenzofuran-7-yl)-2,3,4,5-tetrahydro-1H-3-methyl-3-benzazepine, HCl $^1$H-NMR,δppm. free base (CD$_3$SOCD$_3$, TMS): 2.2 1H(t); 2.3 3H(s); 2.85 3H(s); 3.0 3H(s); 2.6–3.3 7H(m); 4.35 1H(d); 4.4 2H(t); 6.38 1H(s); 6.95 2H(m); 7.2 2H(m).

EXAMPLE 15

(+)-8-chloro-7-[(N,N-diethylamino)carbonyloxy]-5-(2,3-dihydro-benzofuran-7-yl)-2,3,4,5-tetrahydro-1H-3-methyl-3-benzazepine, HCl $^1$H-NMR,δppm. (CD$_3$SOCD$_3$, TMS): 1.15 6H(double t); 2.85 3H(s); 3.0–3.8 12H(m); 4.5 2H(m); 4.85 1H(d); 6.3 1H(s); 7.0 2H(m); 7.3 2H(d);

EXAMPLE 16

(+)-8-chloro-7-[(N-methyl-N-cyclohexyl)amino carbonyloxy]-5-(2,3-dihydro-benzofuran-7-yl)-2,3,4,5-tetrahydro-1H-3-methyl-3-benzazepine, HCl by refluxing 4 h in pyridine.

$^1$H-NMR,δppm. free base (CD$_3$SOCD$_3$, TMS): 1.0–1.8 10H(m); 2.15 1H(t); 2.2 3H(s); 2.7–3.7 11H(m); 4.35 1H(d); 4.45 2H(t); 6.35 1H(s); 6.9 2H(m); 7.2 1H(d); 7.35 1H(s).

EXAMPLE 17

(+)-8-chloro-7-[(N-methyl-N-ethyl)amino carbonyloxy]-5-(2,3-dihydro-benzofuran-7-yl)-2,3,4,5-tetrahydro-1H-3-methyl-benzazepine, HCl by refluxing 8 h in pyridine.

$^1$H-NMR,δppm. free base (CD$_3$SOCD$_3$, TMS): 1.0–1.15 3H(double t, after heating to 90° C. it appears as one t); 2.15 1H(t); 2.25 3H(s); 2.7–3.4 12H(m); 4.4 1H(d); 4.45 2H(t); 6.35 1H(broad s); 6.9 2H(m); 7.2 2H(d).

EXAMPLE 18

(+)-8-chloro-7-[(N-methyl-N-isopropyl)amino carbonyloxy]-5-(2,3-dihydro-benzofuran-7-yl)-2,3,4,5-tetrahydro-1H-3-methyl-3-benzazepine, HCl by refluxing 8 h in pyridine.

$^1$H-NMR,δppm. free base (CD$_3$SOCD$_3$, TMS): 1.0–1.2 6H(double d); 2.15 1H(t); 2.25 3H(s); 2.7–3.25 11H(m); 4.4 1H(d); 4.45 2H(t); 6.3 1H(s); 6.9 2H(m); 7.2 1H(d); 7.4 1H(s).

EXAMPLE 19

(+)-8-chloro-7-[(N-methyl-N-benzyl)amino carbonyloxy]-5-(2,3-dihydro-benzofuran-7-yl)-2,3,4,5-tetrahydro-1H-3-methyl-3benzazepine, HCl $^1$H-NMR,δppm. free base (CD$_3$SOCD$_3$, TMS): 2.25 1H(t); 2.3 3H(s); 2.7–3.3 10H(m); 4.3–4.6 5H(m); 6.3 1H(d); 6.9 2H(m); 7.2–7.5 7H(m).

In analogy with the preparation described in example 5 the following compounds were synthesized:

EXAMPLE 20

(+)-8-chloro-7-[(S)-(2-benzyloxycarbonyl)-1-pyrrolidinylcarbonyloxy]-5-(2,3-dihydro-benzofuran-7-yl)-2,3,4,5-tetrahydro-1H-3-methyl-3-benzazepine by refluxing 4 h in pyridine.

$^1$H-NMR,δppm. (CD$_3$SOCD$_3$, TMS): 1.8–2.0 3H(m); 2.2 2H(s); 2.3 3H(s); 2.8–3.7 10H(m); 4.4–4.55 3H(m); 4.95–5.2 2H(m); 6.45 1H(d); 6.7 1H(s); 6.9 2H(m); 7.2 1H(m); 7.25–7.4 5H(m).

EXAMPLE 21

(+)-8-chloro-7-[(R)-(2-benzyloxycarbonyl)-1-pyrrolidinylcarbonyloxy]-5-(2,3-dihydro-benzofuran-7-yl)-2,3,4,5-tetra-hydro-1H-3-methyl-3-benzazepine by refluxing 4 h in pyridine.

$^1$H-NMR,δppm. (CD$_3$SOCD$_3$, D20, TMS): 1.8–2.0 3H(m); 2.2 2H(s); 2.3 3H(s); 2.8–3.7 10H(m); 4.4–4.55 3H(m); 4.95–5.2 2H(m); 6.45 1H(d); 6.7 1H(s); 6.9 2H(m); 7.2 1H(m); 7.25–7.4 5H(m).

EXAMPLE 22

(+)-8-chloro-7-[(S)-(2-N,N-diethylaminocarbonyl-methyloxycarbonyl)-1-pyrrolidinyl-carbonyloxy]-5-(2,3-dihydro-benzofuran-7-yl)-2,3,4,5-tetrahydro-1H-3-methyl-3-benzazepine by refluxing 4 h in pyridine.

$^1$H-NMR,δppm. (CD3SOCD$_3$, D$_2$O, TMS): 1.0–1.1 6H(double t, after heating to 90° C. it appears as one t); 1.9 2H(m); 2.1–2.3 6H(s,m); 2.6–3.6 13H(m); 4.3–4.55 4H(m); 4.6–4.85 2H(m); 6.35 1H(d); 6.9 2H(m); 7.2 2H(m); 7.4 1H(d).

EXAMPLE 23

(+)-8-chloro-7-[(R)-(2-N,N-diethylaminocarbonyl-methyloxycarbonyl)-1-pyrrolidinyl-carbonyloxy]-5-(2,3-dihydro-benzofuran-7-yl)-2,3,4,5-tetrahydro-1H-3-methyl-3-benzazepine by refluxing 4 h in pyridine.

$^1$H-NMR,δppm. (CD$_3$SOCD$_3$, D$_2$O, TMS). 1.0–1.1 6H(double t, after heating to 90° C. it appears as one t); 1.9 2H(m); 2.1–2.3 6H(s,m); 2.6–3.6 13H(m); 4.3–4.55

4H(m); 4.6–4.85 2H(m); 6.35 1H(d); 6.9 2H(m); 7.2 2H(m); 7.4 1H(d).

EXAMPLE 24

(+)-8-chloro-7-[(S)-(2-carboxy)-1-pyrrolidinyl-carbonyloxy]-5-(2,3-dihydro-benzofuran-7-yl)-2,3,4,5-tetrahydro-1H-3-methyl-3-benzazepine 113 mg (0.2 mmol) of (+)-8-chloro-7-[(S)-(2-benzyloxycarbonyl)-1-pyrrolidinyl-carbonyloxy]-5-(2,3-dihydro-benzofuran-7-yl)-2,3,4,5-tetrahydro-1H-3-methyl-3-benzazepine (example 22) were dissolved in 20 ml tetrahydrofuran. 10 mg palladium/cellite (10%) was added and the suspension was hydrogenated at room temperature and 1 atm. for 45 min. Further 20 mg of palladium/carbon (10%) was added, and the mixture was hydrogenated for 3 h. The catalyst was removed by filtration, and the solvent was evaporated in vacuo. The residual material was dissolved in a few ml of methanol/tetrahydrofuran, water was added and the product was obtained by lyophilyzation.

$^1$H-NMR, ppm. ($CD_3SOCD_3$, $D_2O$, TMS): 1.8–2.0 3H(m); 2.1–2.3 1H(m); 2.25 3H(s); 2.9–4.6 22H(m); 6.45 1H(s); 6.9 2H(d); 7.2 1H(broad s); 7.4 1H(d).

EXAMPLE 25

(+)-8-chloro-7-[(R)-(2-carboxy)-1-pyrrolidinyl-carbonyloxy]-5-(2,3-dihydro-benzofuran-7-yl)-2,3,4,5-tetrahydro-1H-3-methyl-3-benzazepine The compound was prepared in analogy with the preparation described in example 24.

$^1$H-NMR,δppm. ($CD_3SOCD_3$, $H_2O$, TMS): 1.8–2.0 3H(m); 2.1–2.3 1H(m); 2.25 3H(s); 2.9–4.6 22H(m); 6.45 1H(s); 6.9 2H(d); 7.2 1H(broad s); 7.4 1H(d).

In analogy with the preparation described in example 5 the following compounds were synthesized:

EXAMPLE 26

(+)-8-chloro-7-[(S)-(N-methyl-N-(1-methoxycarbonyl-1-phenethyl))amino carbonyloxy]-5-(2,3-dihydro-benzofuran-7-yl)-2,3,4,5-tetrahydro-1H-3-methyl-3-benzazepine by refluxing 4 h in pyridine.

$^1$H-NMR,δppm. ($CD_3SOCD_3$, $D_2O$, TMS): 2.1–2.2 4H(s,t); 2.6–3.2 12H(m); 3.6 3H(d, after heating to 90° C. it appears as s); 4.3–4.5 3H(m); 4.8 1H(m); 6.4 1H(d, after heating to 90° C. it appears as a singlet); 6.85 2H(m); 7.15–7.35 7H(m).

EXAMPLE 27

(+)-8-chloro-7-[(S)-N-methyl-N-(1-N',N'-diethylaminocarbonyl-methyloxycarbonyl-1-phenethyl)amino carbonyloxy]-5-(2,3-dihydro-benzofuran-7-yl)-2,3,4,5-tetrahydro-1H-3-methYl-3benzazepine by refluxing 5 h in pyridine.

$^1$H-NMR,δppm. ($CD_3SOCD_3$, TMS): 0.9–1.1 6H(double t); 2.7–5.1 26H(m); 6.1 1H(s); 6.9–7.5 9H(m).

EXAMPLE 28

(+)-8-chloro-7-[(S)-N-methyl-N-(1-methoxycarbonyl-1-ethyl)amino carbonyloxy]-5-(2,3-dihydro-benzofuran-7-yl)-2,3,4,5-tetrahydro-1H-3-methyl-3-benzazepine by refluxing 6 h in pyridine $^1$H-NMR,δppm ($CD_3SOCD_3$, TMS): 1.4 3H(double d); 2.2 1H(t); 2.25 3H(s); 2.7–3.3 10H(m); 3.6 3H(double s); 4.4 1H(d); 4.5 2H(t); 4.6 1H(m); 6.4 1H(d); 6.9 2H(m); 7.2 1H(d); 7.4 1H(d).

EXAMPLE 29

(+)-8-chloro-7-[N-methyl-N-(benzyloxycarbonyl-methyl)amino carbonyloxy]-5-(2,3-dihydro-benzofuran-7-yl)-2,3,4,5-tetrahydro-1H-3-methyl-3-benzazepine $^1$H-NMR,δppm. ($CD_3SOCD_3$, TMS): 2.1 1H(t); 2.15 3H(s); 2.7–3.4 9H(m); 4.1–4.3 2H(d, after heating to 90° C. it appears as a singlet); 4.4 1H(t); 4.5 2H(t); 5.15 2H(m); 6.4 1H(d); 6.85 2H(m); 7.15 1H(t); 7.35 6H(m).

EXAMPLE 30

(+)-8-chloro-7-[N-methyl-N-(methoxycarbonyl-methyl)amino carbonyloxy]-5-(2,3-dihydrobenzofuran-7-yl)-2,3,4,5-tetrahydro-1H-3-methyl-3-benzazepine $^1$H-NMR,δppm. ($CD_3SOCD_3$, TMS): 2.2 1H(t); 2.3 3H(s); 2.8–3.3 10H(m); 3.65 3H(d); 4.15 2H(d); 4.4 1H(t); 4.5 2H(t); 6.4 1H(d); 6.9 2H(m); 7.2 1H(d); 7.4 1H(d).

EXAMPLE 31

(+)-8-chloro-7-[(R,S)-N-methyl-N-(1-methoxycarbonyl-1-ethyl)amino carbonyloxy]-5-(2,3-dihydro-benzofuran-7-yl)-2,3,4,5-tetrahydro-1H-3-methyl-3-benzazepine by refluxing 6 h in pyrididne.

$^1$H-NMR,δppm. ($CD_3SOCD_3$, TMS): 1.4 3H(double d); 2.2 1H(t); 2.3 3H(s); 2.8–3.4 10H(m); 3.6 3H(t); 4.4 1H(d); 4.5 2H(t); 4.6 1H(m); 6.4 1H(d); 6.9 2H(m); 7.2 1H(d); 7.4 1H(d).

EXAMPLE 32

(+)-8-chloro-7-[(N-methyl-N-carboxymethyl)amino carbonyloxy]-5-(2,3-dihydro-benzofuran-7-yl)-2,3,4,5-tetrahydro-1H-3-methyl-3-benzazepine, HCl The compound was prepared in analogy with the preparation described in example 26 by hydrogenation for 10 h using the hydrochloride salt of (+)-8-chloro-7-[N-methyl-N-(benzyloxycarbonyl-methyl)amino carbonyloxy]-5-(2,3-dihydro-benzofuran-7-yl)-2,3,4,5-tetrahydro-1H-3-methyl-3-benzazepine $^1$H-NMR,δppm. ($CD_3SOCD_3$, TMS): 2.75 3H(s); 2.8–3.0 3H(2s); 3.1–3.6 8H(m); 3.9–4.1 2H(2s); 4.5 2H(m); 4.8 1H(s); 6.35 1H(s); 6.9 2H(d); 7.3 1H(d); 7.5 1H(d).

EXAMPLE 33

Tablets are prepared by methods known to professionals skilled in the art, the composition of each tablet being:

| Formulation, tablets | mg/tablet |
| --- | --- |
| Benzazepine | 50 |
| Lactose | 120 |
| Avicel (PH 101) | 40 |
| Kollidon K25 | 5 |
| Talcum | 4 |
| Magnesium stearate | 1 |
| Tablet weight | 220 |

The bioavailability of the prodrugs described in Examples 1–32, measured in mongrel dogs in accordance with the previously indicated method, are presented in the below indicated table.

TABLE

| Example No. | R⁵ | R⁸ | R⁹ | Absolute bioavailability, F (%) |
|---|---|---|---|---|
| Example 1 | benzofuran-O- | —CH₃ | —CH₃ | 20 |
| Example 4 | benzofuran-O- | —H | —CH(CH₃)—C(=O)—OCH₃ | 40 |
| Example 6 | benzofuran-O- | —H | —CH(CH₃)₂ | 15 |
| Example 7 | benzofuran-O- | —H | —CH₂—CH=CH₂ | 24 |
| Example 8 | benzofuran-O- | —H | —CH₂—C₆H₅ | 5 |
| Example 10 | benzofuran-O- | —H | —C₆H₁₁ (cyclohexyl) | 6 |
| Example 11 | benzofuran-O- | —H | —CH(CH₂C₆H₅)—C(=O)—OCH₃ | 7 |
| Example 12 | benzofuran-O- | —H | —CH(CH(CH₃)CH₂CH₃)—C(=O)—OCH₃ | 11 |
| Example 13 | benzofuran-O- | —H | —CH(CH₂CH(CH₃)₂)—C(=O)—OCH₃ | 7 |

As an average, the absolute bioavailability of the parent compounds in mongrel dogs is around 5%.

We claim:

1. Carbamic acid esters selected from 7-hydroxy-2,3,4,5-tetrahydro-1H-3-benzazepines having the formula I

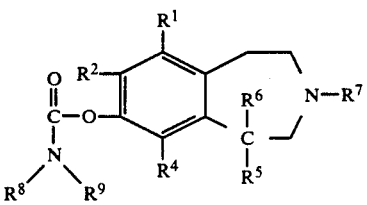

(I)

wherein
R¹ is H, halogen, or C₁₋₄ alkyl
R² is halogen, CF₃, CN $R^4$ is H, or halogen $R^5$ is selected from the group consisting of benzofuranyl and 2,3-dihydrobenzofuranyl, $R^6$ is H or $CH_3$ $R^7$ is H or $C_{1-4}$ alkyl $R^8$ is H, alkyl, alkenyl, phenylalkyl, cycloalkyl, or phenyl $R^9$ is H, or $R^9$ together with $R^8$ forms the remainder of piperidino, pyrrolidinyl, morpholino, piperazinyl, or

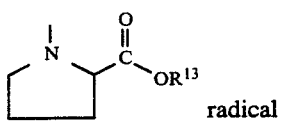 radical or $R^9$ can be alkyl or alkoxycarbonyl with the formula

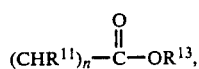

wherein n is 0 or 1, where $R^{11}$ is H, $CH_3$, $(CH_3)_2CH$, $CH_2CH(CH_3)_2$,

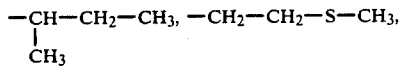

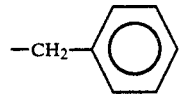

and $R^{13}$ is H, alkyl, cycloalkyl, aralkyl, or a 2-acetamide group with the formula

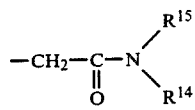

where
$R^{15}$ is H, $CH_3$, $C_2H_5$, $C_3H_8$, or $CH(CH_3)_2$, and
$R^{14}$ is H, $CH_3$, $C_2H_5$, $C_3H_8$ or $CH(CH_3)_2$,
and pharmaceutically-acceptable salts thereof, provided that $R^8$ cannot be benzyl when $R^9$ is hydrogen.

2. A compound of claim 1, wherein the substituent $R^5$ is benzofuranyl.

3. A compound according to claim 1, which is (+)-8-chloro-7[(N,N-dimethylamino)carbonyloxy]-5-(7-benzofuranyl)-2,3,4,5-tetrahydro-1H-3-methyl-3-benzazepine.

4. A compound according to claim 1., which is (+)-8-chloro-7[(R,S)-N-(1-methoxycarbonyl-1-ethyl)amino carbonyloxy]-5-(7-benzofuranyl)-2,3,4,5-tetrahydro-1H-3-methyl-3-benzazepine.

5. A compound according to claim 1, which is (+)-8-chloro-7-[(S)-N-(1-methoxycarbonyl-2-methyl-butyl)aminocarbonyloxy]-5-(7-benzofuranyl)-2,3,4,5-tetrahydro-1H-3-methyl-3-benzazepine.

6. A compound according to claim 1, which is (+)-8-chloro-7-(allylaminocarbonyloxy)-5-(7-benzofuranyl)-2,3,4,5-tetrahydro-1H-3-methyl-3-benzazepine.

7. A compound according to claim 1, which is (+)-8-chloro-7-(isopropylaminocarbonyloxy)-5-(7-benzofuranyl)-2,3,4,5-tetrahydro-1H-3-methyl-3-benzazepine.

8. A pharmaceutical composition suitable for use in the treatment of a mental disorder comprising an amount of a compound of claim 1 which is effective for the alleviation of such disorder together with a pharmaceutically-acceptable carrier or diluent.

9. A method of treating a mental disorder in a subject in need of such treatment comprising the step of administering to the said subject an amount of a compound of claim 1 which is effective for the alleviation of such ailment.

10. A method of claim 9 wherein the compound is administered in the form of a pharmaceutical composition thereof, in which it is present together with a pharmaceutically-acceptable carrier or diluent.

* * * * *

UNITED STATES PATENT AND TRADEMARK OFFICE
CERTIFICATE OF CORRECTION

PATENT NO. : 5,017,571

DATED : May 21, 1991

INVENTOR(S) : Kristian T. Hansen, Hans Bundgaard, Peter Faarup

It is certified that error appears in the above-identified patent and that said Letters Patent is hereby corrected as shown below:

Column 2, approximate line 7; "with form" should read
-- with $R^8$ form --.
Column 2, approximate line 24; "is O is 1," should read
-- is O or 1, --. (R&A 7-23-90, P.1)
Column 3, line 34; "invention and" should read
-- invention $R^8$ and --.
Column 3, approximate line 62; "for, the" should read --for the --.
Column 5, line 61; "solution re-" should read --solution, re- --.
Column 6, approximately line 8; "[(N" should read -- [(N, --.
Column 6, line 13; "chloro7" should read -- chloro-7 --.
Column 6, line 14; "-methyl3-" should read -- -methyl-3- --.
Column 6, approximately line 28; "method see" should read
-- method, see --.
Column 7, line 4/5; "-2 3 4 5-" should read-- -2,3,4,5- --.
Column 7, line 7; "-7-5-" should read -- -7-hydroxy-5- --.
Column 7, approximately line 17; "IN" should read -- 1N --.
Column 7, approximately line 26/27; move the closing parenthesis
")" before "amino" to the line above after "ethyl" and
before the dash.
Column 8, line 2; "4.80   H" should read -- 4.80 1H --.
Column 9, line 3/4; move the closing parenthesis ")" before "amino"
to the line above after "phenethyl" and before the dash.

UNITED STATES PATENT AND TRADEMARK OFFICE
CERTIFICATE OF CORRECTION

PATENT NO. : 5,017,571

DATED : May 21, 1991

INVENTOR(S) : Kristian T. Hansen, Hans Bundgaard, Peter Faarup

It is certified that error appears in the above-identified patent and that said Letters Patent is hereby corrected as shown below:

Column 9, approximately line 42; "carbonYloxy]" should read
  -- carbonyloxy] --.
Column 9, approximately line 44; "methYl" should read --methyl--.
Column 9, approximately line 63; "methyl-benzazepine," should
  read -- methyl -3-benzazepine, --.
Column 10, approximately line 18;"-3benzazepine," should read
  -- -3-benzazepine, --.
Column 11, approximately line 53; move the closing parenthesis
  ")" before "amino" to the line above after "phenethyl" and
  before the dash.
Column 11, line 55; "-methYl-3benzazepine" should read
  -- -methyl-3-benzazepine --.
Column 16, line 15; "-7[" should read -- -7-[ --.( R&A 7-23-90,P.2)

Signed and Sealed this

Twentieth Day of October, 1992

*Attest:*

DOUGLAS B. COMER

*Attesting Officer*   *Acting Commissioner of Patents and Trademarks*